United States Patent
Flashaar et al.

(10) Patent No.: US 11,332,266 B2
(45) Date of Patent: May 17, 2022

(54) METHOD FOR DISINFECTING A WATER SYSTEM OF AN AIRCRAFT

(71) Applicant: Airbus Operations GmbH, Hamburg (DE)

(72) Inventors: Sebastian Flashaar, Hamburg (DE); Michael Rempe, Hamburg (DE); Axel Schreiner, Hamburg (DE)

(73) Assignee: Airbus Operations GmbH

( * ) Notice: Subject to any disclaimer, the term of this patent is extended or adjusted under 35 U.S.C. 154(b) by 286 days.

(21) Appl. No.: 16/417,887

(22) Filed: May 21, 2019

(65) Prior Publication Data

US 2019/0367189 A1 Dec. 5, 2019

(30) Foreign Application Priority Data

May 30, 2018 (DE) ...................... 10 2018 208 611.7

(51) Int. Cl.
*B64F 5/30* (2017.01)
*A61L 2/07* (2006.01)

(52) U.S. Cl.
CPC . *B64F 5/30* (2017.01); *A61L 2/07* (2013.01)

(58) Field of Classification Search
CPC ...... B64F 5/30; B64F 1/36; A61L 2/07; A61L 2/06; Y02P 70/50; B64D 11/02; B64D 11/04; C02F 2307/14; C02F 1/025; C02F 2201/001; B08B 9/00; B08B 9/0327
See application file for complete search history.

(56) References Cited

U.S. PATENT DOCUMENTS

| 5,381,987 | A | 1/1995 | Carns |
| 8,083,861 | B2 * | 12/2011 | Labib .................... B08B 9/0326 |
| | | | 134/22.1 |
| 8,858,878 | B2 * | 10/2014 | Risch ........................ C02F 1/50 |
| | | | 422/26 |
| 10,131,554 | B2 | 11/2018 | Reiss et al. |
| 10,766,058 | B2 | 9/2020 | Boukari |

(Continued)

FOREIGN PATENT DOCUMENTS

| DE | 102009009938 A1 | 8/2010 |
| DE | 102010018273 A1 | 10/2011 |

(Continued)

OTHER PUBLICATIONS

Deutscher Verein des Gas- und Wasserfaches (DVGW), "Reinigung und Desinfektion von Trinkwasser-Installationen," Worksheet W 557, Oct. 2012 [publication from the German Association for the Gas and Water Sector (DVGW) entitled "Cleaning and Disinfection of Drinking Water Installations", Worksheet W 557, Oct. 2012].

(Continued)

*Primary Examiner* — Regina M Yoo
(74) *Attorney, Agent, or Firm* — Lerner, David, Littenberg, Krumholz & Mentlik, LLP

(57) ABSTRACT

A method for disinfecting a water system of an aircraft includes the introduction of damp hot air at an inlet of the water system by a ground service unit; flushing of the damp hot air from the inlet through water pipes of the water system to an outlet of the water system; and extraction of the damp hot air at the outlet; wherein the damp hot air is flushed into the inlet and out of the outlet over a predefined disinfection period, and wherein the damp hot air has a temperature between 60° C. and 80° C.

10 Claims, 4 Drawing Sheets

(56) References Cited

U.S. PATENT DOCUMENTS

| | | | |
|---|---|---|---|
| 11,000,041 B2* | 5/2021 | Benisti | A01N 59/08 |
| 2004/0217183 A1 | 11/2004 | Bae et al. | |
| 2005/0103726 A1* | 5/2005 | Palm | C02F 1/78 |
| | | | 210/760 |
| 2005/0126927 A1* | 6/2005 | Lindauer | C02F 1/4674 |
| | | | 205/743 |
| 2013/0094994 A1 | 4/2013 | Risch et al. | |
| 2014/0230845 A1 | 8/2014 | Boukari | |
| 2016/0236247 A1 | 8/2016 | Boukari | |
| 2016/0251090 A1 | 9/2016 | Boukari | |
| 2018/0085796 A1 | 3/2018 | Boukari | |
| 2018/0334402 A1* | 11/2018 | Williams | B01D 35/30 |
| 2018/0360047 A1* | 12/2018 | Benisti | A01N 25/22 |

FOREIGN PATENT DOCUMENTS

| | | | |
|---|---|---|---|
| EP | 1025917 A1 | 8/2000 | |
| FR | 2975928 A1 | 12/2012 | |
| FR | 3008632 A1 | 1/2015 | |
| WO | 2006100094 A1 | 9/2006 | |
| WO | 2010142924 A2 | 12/2010 | |
| WO | 2018234218 A1 | 12/2018 | |

OTHER PUBLICATIONS

Co-Pending U.S. Appl. No. 16/419,200, filed May 22, 2019.
Search Report for GB1907607.4 dated Nov. 14, 2019.
Search Report for GB1907608.2 dated Nov. 20, 2019.
German Search Report for Application No. 102018208611.7 dated Mar. 29, 2019, 8 pages (p. 2 categorizing the cited references).

* cited by examiner

METHOD FOR DISINFECTING A WATER SYSTEM OF AN AIRCRAFT

FIELD OF THE INVENTION

The present invention concerns a method for disinfecting a water system of an aircraft.

BACKGROUND OF THE INVENTION (Drinking) water systems of modern passenger aircraft typically comprise an extensive network of water pipes which extend from the inlet and outlet openings on the exterior of the aircraft fuselage, via distribution pipes through the aircraft fuselage, to consumers such as the galley, sanitary facilities etc. inside a passenger cabin. In addition, such passenger aircraft normally have at least one water tank for supplying the water system, which for example may have a capacity of around 1000 L.

The publication from the German Association for the Gas and Water Sector (DVGW) entitled "Cleaning and Disinfection of Drinking Water Installations", Worksheet W 557, October 2012, describes the practical performance of cleaning and disinfection measures, and preventative measures to prevent contamination of drinking water installations. One possibility for disinfection is thermal disinfection in which hot water is flushed through a complete drinking water installation. Another possibility for disinfection, which has become widely used in particular in the aviation sector, is chemical disinfection in which disinfectant chemicals, such as for example sodium hypochloride, chlorine dioxide and hydrogen peroxide, are used in specific application concentrations to treat the drinking water installation. Furthermore, in particular in medical and industrial applications, it is proposed to use hot water vapour at the water boiling point (e.g. 100° C. at 1 atm) for disinfection.

Normally, ground service equipment (GSE), such as for example tankers with sufficiently large tanks, is used for thermal and chemical disinfection of the water tank of passenger aircraft; these units provide a corresponding quantity of a hot water store or disinfectant mixture so that the aircraft water tank, the connecting supply and outlet lines, and the aircraft's pipe network can be completely filled with the fluid. For this, large quantities of fluid must be provided and in some cases heated. In addition, it may be necessary to flush the water tank and/or water pipes several times, whereby disinfection and any associated purging etc. may take a whole day.

BRIEF SUMMARY OF THE INVENTION

Aspects of the present invention may provide simpler, faster and cheaper solutions for disinfecting water systems of aircraft.

Accordingly, a method is provided for disinfecting a water system, in particular a drinking water system, of an aircraft. The method comprises the introduction of damp hot air at an inlet of the water system by a ground service unit; flushing of the damp hot air from the inlet through water pipes of the water system to an outlet of the water system; and extraction of the damp hot air at the outlet; wherein the damp hot air is flushed into the inlet and out of the outlet over a predefined disinfection period; and wherein the damp hot air has a temperature between 60° C. and 80° C.

A concept forming a basis of the present invention is to avoid the use of both chemicals and storage tanks, in that damp hot air is introduced directly into the pipes to be disinfected, on site, by a ground service unit (GSE). For this, a GSE requires only a connection to a supply for the damp hot air or a corresponding device for producing this. In the present method, there is no need for a large fluid tank which can only be heated with high energy consumption. The GSE may therefore be designed compactly so as to be mobile and versatile, whereby the disinfection process may be used selectively in certain critical (pipe) regions in a time-saving, cost-saving and energy-saving fashion. Furthermore, because of the compact design of the GSE and the merely small (electrical) power consumption, a (mobile) use in an aviation-specific working environment becomes easier or economically practicable. The use of damp hot air also offers a considerable advantage over the use of hot water in terms of time and energy. This is partly because, by means of the air, surfaces can be heated and hence disinfected in a targeted fashion without the volumes enclosed by the surfaces also having to be heated and fluid-filled accordingly, whereby a particular advantage of the method is found in the disinfection of large-volume aircraft drinking water tanks. Bacteria and other germs in fact settle primarily on the (inner) surfaces of the pipes or tank.

Firstly, a disinfection process is faster, the higher the water temperature. Secondly, the aircraft components of modern lightweight aircraft frequently only have a limited temperature resistance, which excludes water temperatures of 80° C. or more, in particular boiling water. Accordingly, in this refinement, an advantageous compromise is found between as brief a disinfection period as possible and the least possible deterioration of the affected aircraft structures such as pipes and surrounding regions. In particular, it has been found that the damp hot air has a temperature of at least 60° C. in the entire flushed region of the water pipes. For example, the damp hot air may be provided at a temperature of around 70° C. and flushed through the water pipes. Thus, in particular, the use of water vapour at 100° C. or more is avoided, which could damage or at least adversely affect adjacent aircraft structures.

In a method according to the present invention, in particular damp hot air is used, i.e. hot air with a significant proportion of water vapour—as distinct from dry hot air—in order to create a (convective) flow of a medium with sufficient specific enthalpy for efficient disinfection of pipe and/or tank surfaces at relatively low temperatures between 60° C. and 80° C. In contrast to damp air, dry air would create a lower level of enthalpy, whereby disinfection with dry air would not be efficient at such low temperatures. This is partly because of the amount of water vapour in the damp hot air which leads to condensation on the heated surfaces of the water pipes or tank, whereby these are heated more rapidly. For example, the air could be (completely) saturated or supersaturated damp air, i.e. air with saturated water vapour and in some cases mist droplets, i.e. with a relative humidity of 100% or more. In principle however, variants of the invention are also conceivable in which a high relative humidity of less than 100% is present without the air needing to be completely saturated with water vapour.

In the present case, a distinction is made between disinfection and sterilization. Disinfection in the context of the description means an effect on a water supply system or a medium such as drinking water such that this assumes a state in which it can no longer cause infection. Disinfection of drinking water systems in this sense may be carried out at significantly lower temperatures than the boiling point of water, in particular at temperatures down to around 60° C. In contrast, sterilization means not only an adequate reduction or elimination of germs and pathogens, but also a practically complete removal or elimination of all microorganisms in every development stage, including their rest stages (e.g. spores). Sterilization is therefore typically performed at very high temperatures, e.g. 121° C., not least in order to keep the necessary processing duration as short as possible (e.g. 3 minutes at 121° C.).

Advantageous embodiments and refinements arise from the further subclaims and from the description with reference to the figures.

According to a refinement, the damp hot air may be provided at the inlet as air saturated, in particular completely, with water vapour or air supersaturated with water vapour. In this refinement therefore, because of the condensation of the water vapour on surfaces of the water pipes and/or tank, energy is transmitted particularly efficiently for disinfection.

According to a refinement, the damp hot air may be produced by the ground service unit. To provide the damp hot air, only small quantities of energy are required, so that it can easily be produced directly on site by a compact ground surface unit with little power consumption; in particular, this facilitates use in an aviation-specific working environment or makes this economically practicable.

According to a refinement, the damp hot air may be produced by mixing hot water vapour with compressed air. For example, a ground service unit may have a water connection which is connected to a steam generator for producing a steam jet. At the same time, the ground service unit may be connected to a compressed air supply, via which a compressed air jet is provided which can be mixed with the steam jet in the ground service unit.

According to a refinement, the damp hot air may be produced by heating a water-compressed air mixture. Alternatively or in addition to a mixture of water vapour and compressed air, the damp hot air may also be produced directly by heating a water-air mixture.

According to a refinement, condensed water may be captured at the outlet by a treatment device and recycled to provide the damp hot air. In this refinement, the treatment device thus functions as a condensate recycler. For maximum efficiency in terms of energy and materials, effectively a type of heating circuit may be created from an inlet via the water pipes to an outlet and from there back to the inlet.

According to a refinement, waste heat from the extracted damp hot air may be recycled by a treatment device to provide the damp hot air. In this refinement, the treatment device functions as a heat exchanger.

According to a refinement, the water pipes may comprise inlet pipes, distribution pipes, supply pipes, outlet pipes and/or consumer pipes. In addition, the water pipes may comprise tapping points or similar. For example, flushing may take place not only of the inlet and outlet pipes connected to an inlet or outlet, and the supply or distribution pipes connected thereto and running for example below a cabin floor. Also, consumer pipes, connected to the supply pipes, of consumers, e.g. galleys, sanitary facilities etc., inside a passenger cabin, a cockpit and/or a cargo hold may be disinfected.

According to a refinement, the damp hot air may be flushed through a tank portion of the water system. In this advantageous refinement, a tank portion including one or more tanks is thus flushed solely with damp hot air. The tank or tanks need not be filled with hot water or other fluid in a time- and energy-intensive fashion, which could be impracticable in particular for tanks with a capacity of 1000 L or more, or could hinder use in an aviation-specific working environment. Here, the invention exploits the fact that, typically, it may be sufficient for disinfection if the surfaces of the pipes and tanks on which bacteria and germs primarily settle are adequately heated, e.g. to temperatures between 60° C. and 80° C., e.g. 70° C.

According to a refinement, a tank outlet of the tank portion may be used as the inlet or outlet. For example, an overflow drain or overflow outlet of a tank portion may be used to this purpose. In addition, for example, an inlet of the aircraft which, like the tank outlet, exists as standard may be used as the inlet. Thus no special aircraft-side precautions need be taken to implement the air circulation through the tank portion, or it may be sufficient to make suitable use of the technical facilities of the water system (e.g. pipes, valves etc.) which are present in any case.

The above embodiments and refinements may be combined arbitrarily with each other where suitable. Further possible embodiments, refinements and implementations of the invention also include combinations, not explicitly cited, of features of the invention described above or below in relation to exemplary embodiments. In particular, the person skilled in the art will also add individual aspects to the respective basic embodiment of the present invention as improvements or additions.

BRIEF DESCRIPTION OF THE DRAWINGS

The present invention is explained in more detail below with reference to the exemplary embodiments indicated in the diagrammatic figures. The drawings show.

DETAILED DESCRIPTION

Figure 1:
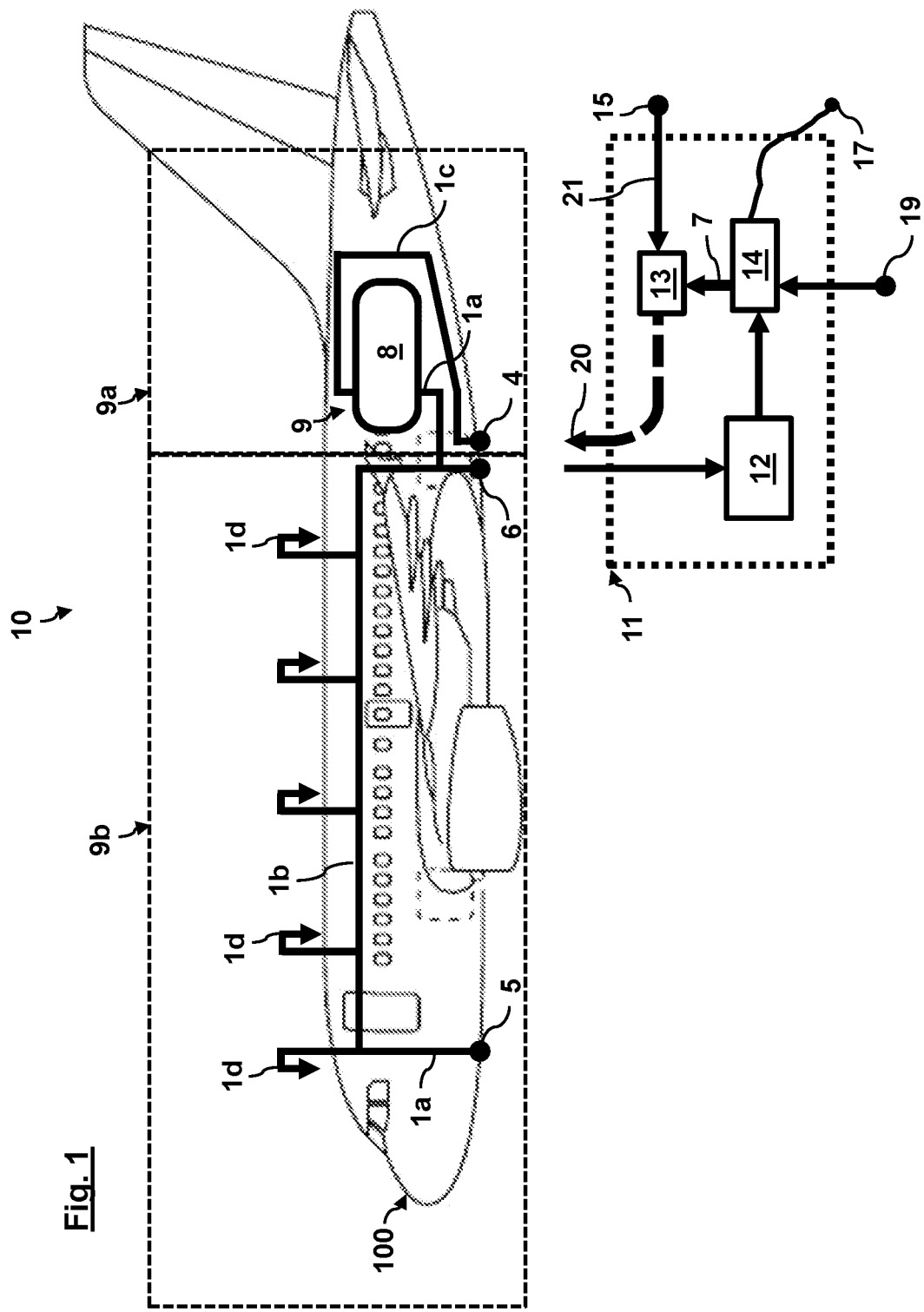
FIG. 1 a diagrammatic side view of an aircraft with a water system before performance of a method for disinfection according to an embodiment of the invention.

The attached figures serve to provide a further understanding of the embodiments of the invention. They illustrate embodiments and, in connection with the description, serve to explain principles and concepts of the invention. Other embodiments and many of the advantages described arise in relation to the drawings. The elements of the drawings are not necessarily shown true to scale.

In the figures of the drawing, the same elements, features and components and those with similar function or effect carry the same reference signs unless specified otherwise.

Figure 2:
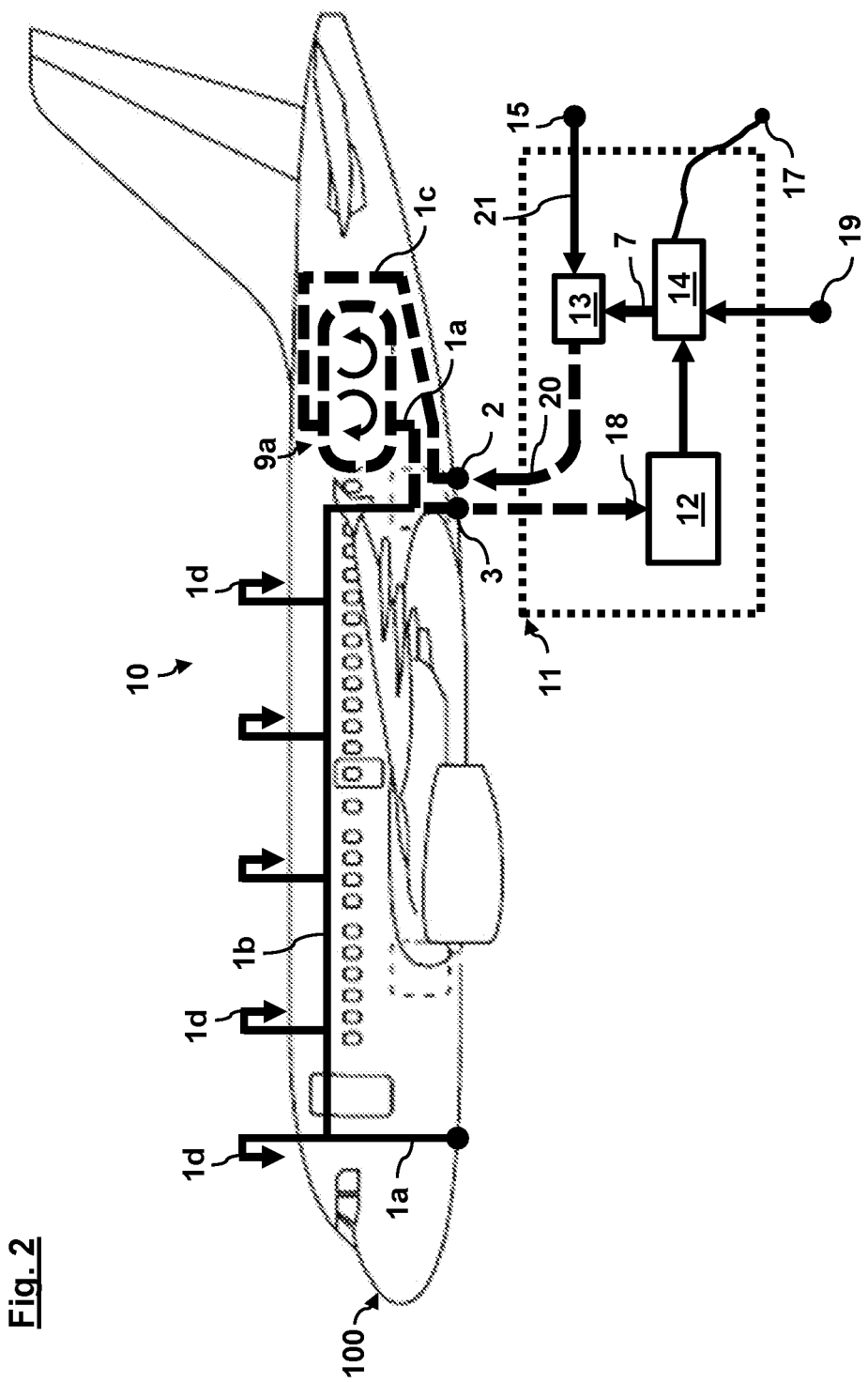
FIG. 2 a diagrammatic side view of the aircraft from FIG. 1 during performance of the method.
Figure 4:
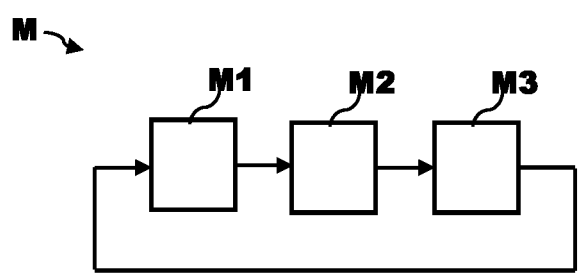
FIG. 4 a diagrammatic flow diagram of a method for disinfection of a water system of an aircraft according to an embodiment of the invention.

FIGS. 1 and 2 show diagrammatic side views of an aircraft 100 with a water system 10 during performance of a disinfection method M according to one embodiment of the invention. A diagrammatic flow diagram of the method M is shown in FIG. 4.

The aircraft 100, e.g. a passenger aircraft, comprises a water system 10, in particular a drinking water system, with a network of water pipes 1a-d and a tank 8 which is situated in a tank portion 9a of the water system 10. The aircraft 100 comprises, in purely exemplary fashion, a front water connection 5 and a rear water connection 6, which in principle may be used as an inlet and/or outlet respectively. Various water pipes 1a-d, including inlet pipes 1a, distribution pipes or supply pipes 1b, outlet pipes 1c and consumer pipes 1d, run from the water connections 5, 6 through a fuselage of the aircraft 100 both in the tank portion 9a and in an adjacent distribution portion 9b. The consumer pipes 1d may here for example lead to consumers in a passenger cabin, a cockpit or a cargo hold etc., e.g. to a galley, sanitary facilities such as a shower, washroom, toilet or similar. The distribution pipes or supply pipes 1b may for example run along and beneath a cabin floor (not shown) and again be connected to the inlet pipes 1a and outlet pipes 1c, which in turn lead to the water connections 5, 6. The tank portion 9a of the water system 10 is furthermore also connected to the water pipes 1a-d of the distribution portion 9b of the water system 10. In addition, the tank portion 9a has a separate tank outflow 4 configured as an overflow or purge connection of the tank 8. The tank 8 may for example have a capacity of 1000 L or more. In principle, it is pointed out that the water connections 5, 6, or the tank outflows 4, water pipes 1a-d and the tank 8 which are shown concretely in this exemplary embodiment, should be regarded as purely exemplary. On the basis of the present teaching, the person skilled in the art will directly conclude that the specific configuration of these components may be structured differently in alternative embodiments. For example, more than two water connections 5, 6 may be provided, the courses of the water pipes 1a-d and their connecting points may be different, or more than one tank 8 may be fitted etc. Furthermore, the tank 8 or the tank portion 9a may be situated at a different position inside the aircraft 100.

FIG. 1 furthermore shows a ground service unit 11, e.g. a ground vehicle. The ground service unit 11 comprises a steam generator 14 which is supplied with electrical energy via a power supply 17. The steam generator 14 is connected to a water supply 19 and vaporises the water supplied by the water supply 19. The water vapour 7 produced is conducted to a steam-air mixer 13 of the ground service unit 11, in which the water vapour 7 is mixed with compressed air 21 from a compressed air supply 15 to form damp hot air 20, which is completely saturated or supersaturated with water vapour 22 and has a temperature between 60° C. and 80° C., e.g. 70° C. The damp hot air 20 may be used by the ground service unit 11 to fill the water system 10 of the aircraft 100 (see FIG. 2). The ground service unit 11 furthermore has a treatment device 12 which is configured to capture hot condensed water and supply this to the steam generator 14, i.e. the treatment device 12 may act as a condensate recycler. Alternatively or additionally, the treatment device 12 may be configured as a heat exchanger for recycling waste heat from the extracted damp hot air 20, for providing the damp hot air 20 (e.g. for preheating compressed air and water). The use of this arrangement in a method M for disinfecting the water system 10 of the aircraft 100 is explained below with reference to FIG. 2.

In FIG. 2, the ground surface unit 11 is connected to the tank outlet 4 for introducing the damp hot air 20, and to the rear water connection 6 for receiving condensed water 18 or recovering waste heat from the extracted damp hot air 20. The rear water connection 6 is here used as an outlet 3 for the condensed water 18, while the tank outlet 4 in this example serves as the inlet 2.

In the example of FIGS. 1 and 2, the water system 10 of the aircraft 100 is disinfected, in that during step M1, the damp hot air 20 is introduced at an inlet 2 by the ground service unit 11, then flushed from the inlet 2 through water pipes 1a, 1c and the tank 8 of the tank portion 9a to the outlet 3, and extracted again at the outlet by the ground service unit 11. The flow of damp hot air 20 is indicated in FIG. 2 by thick dotted lines. This flushing process is carried out over a predefined disinfection period. The damp hot air 20 is conducted into the tank 8 such that the air 20 circulates in the tank 8 as extensively and/or turbulently as possible (indicated by arrows in FIG. 2). Because of the complete saturation or supersaturation with water vapour, the water vapour in the hot damp air 20 condenses onto surfaces of the water pipes 1a, 1c and the tank 8, e.g. a tank wall (not shown).

Because of the high enthalpy density of the damp hot air 20, these surfaces are heated particularly quickly and efficiently to a predefined temperature between 60° C. and 80° C., e.g. 70° C. At the same time, there is no need to fill the tank 8 completely with a liquid which would also have to be heated in an energy-intensive fashion. As a result, the method M can be implemented particularly quickly, economically and energy-efficiently. Surfaces can be heated and hence disinfected with the damp hot air in a targeted fashion, without the volumes enclosed by the surfaces also having to be filled with water and heated to the same extent. Bacteria and other germs primarily settle on the inner surfaces of the water pipes 1a, 1c or tank 8. The ground service unit 11 used may be designed compactly so as to be mobile, since no external fluid tanks or high-power heating devices are required (which facilitates use in an aviation-specific working environment or makes this economically practicable for the first time). These advantages become all the greater, the larger the tank 8 of the aircraft 100. In addition, the use of water vapour in the region of the water boiling point, e.g. 100° C. or more, is avoided, whereby adverse effects or damage to the affected aircraft structures, such as the water pipes 1a, 1c and surrounding regions, can be excluded.

Figure 3:
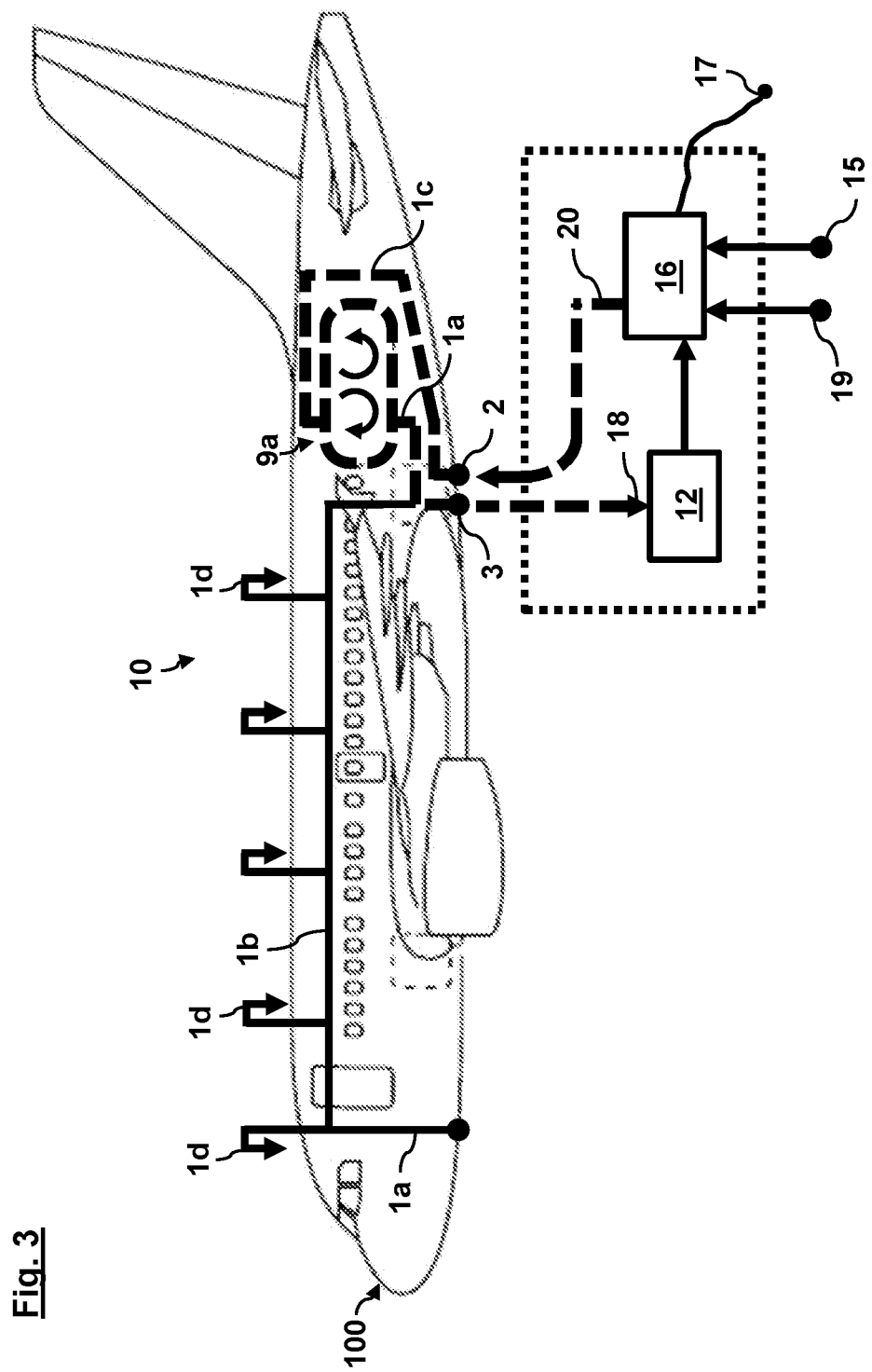
FIG. 3 a diagrammatic side view of an aircraft with a water system during performance of a method for disinfection according to a further embodiment of the invention.

An alternative exemplary variant of the method M is shown in FIG. 3, wherein the aircraft 100 and its water system 10 are configured identically to that in FIGS. 1 and 2. In contrast to the embodiment in FIGS. 1 and 2, the ground service unit 11 here comprises a heating device 16 which is supplied both with water from a water supply 19 and with compressed air from a compressed air supply 15. A water-compressed air mixture, produced by mixing water and compressed air, is heated by the heating device 16, producing damp hot air 20 which is completely saturated or supersaturated with water vapour and has a temperature in the range between 60° C. and 80° C., e.g. 70° C. Thus an alternative variant is provided for producing the damp hot air 20 in the ground service unit 11. Apart from these differences, the method M resembles that in FIGS. 1 and 2.

In the above detailed description, various features have been combined in one or more examples to improve the clarity of the depiction. It should however be clear that the above description is merely illustrative but not restrictive in nature. It serves to cover all alternatives, modifications and equivalents of the various features and exemplary embodiments. Many other examples will be immediately and directly evident, in the light of the above description, to the person skilled in the art because of his professional knowledge.

For example, the number of connections used, the flow direction of the hot water and the course of the water pipes may be adapted to the existing configurations of the aircraft to be disinfected.

The exemplary embodiments have been selected and described to illustrate as well as possible the principles on which the invention is based and its possible applications in practice. Thus skilled persons may use and modify the invention and its various exemplary embodiments optimally in relation to the proposed application. In the claims and description, the terms "containing" and "including" are used as neutral linguistic concepts for the corresponding term "comprising". Furthermore, use of the terms "one" or "a" does not in principle exclude a plurality of the features and components thus described.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

LIST OF REFERENCE SIGNS 1a-d Water pipe
1a Inlet pipe
1b Distribution pipe
1c Outlet pipe
1d Consumer pipe
2 Inlet
3 Outlet
4 Tank outlet
5 Front water connection
6 Rear water connection
7 Water vapour
8 Tank
9a Tank portion/rear portion
9b Distribution portion
10 Water system
11 Ground service unit
12 Treatment device
13 Steam-air mixer
14 Steam generator
15 Compressed air supply
16 Heater device
17 Power supply
18 Condensed water
19 Water supply
20 Damp hot air
21 Compressed air
100 Aircraft
M Method
M1 Method step
M2 Method step
M3 Method step

The invention claimed is:

1. A method for disinfecting a water system of an aircraft, comprising:
   introducing damp hot air at an inlet of the water system by a ground service unit;
   flushing of the damp hot air from the inlet through water pipes of the water system to an outlet of the water system; and
   extracting the damp hot air at the outlet;
   wherein the damp hot air is flushed into the inlet and out of the outlet over a predefined disinfection period; and
   wherein the damp hot air has a temperature between 60° C. and 80° C.

2. The method according to claim 1, wherein the damp hot air is provided at the inlet as air saturated with water vapour or air supersaturated with water vapour.

3. The method according to claim 1, wherein the damp hot air is produced by the ground service unit.

4. The method according to claim 1, wherein the damp hot air is produced by mixing hot water vapour with compressed air.

5. The method according to claim 1, wherein the damp hot air is produced by heating a water-compressed air mixture.

6. The method according to claim 1, wherein condensed water is captured at the outlet by a treatment device and recycled to provide the damp hot air.

7. The method according to claim 1, wherein waste heat from the extracted damp hot air is recycled by a treatment device to provide the damp hot air.

8. The method according to claim 1, wherein the water pipes comprise at least one of inlet pipes, distribution pipes, outlet pipes and consumer pipes.

9. The method according to claim 1, wherein the damp hot air is flushed through a tank portion of the water system.

10. The method according to claim 9, wherein a tank outlet of the tank portion is used as the inlet or outlet.

* * * * *